United States Patent [19]

Pickenhagen et al.

[11] 4,387,248
[45] Jun. 7, 1983

[54] α,β-UNSATURATED ALDEHYDES AND USE OF SAME AS FLAVORING INGREDIENTS

[75] Inventors: Wilhelm Pickenhagen, Chavannes-des-Bois, Switzerland; Alain Velluz, Reignier, France

[73] Assignee: Firmenich SA, Geneva, Switzerland

[21] Appl. No.: 314,446

[22] Filed: Oct. 23, 1981

Related U.S. Application Data

[62] Division of Ser. No. 51,506, Jun. 25, 1979, Pat. No. 4,324,809.

[30] Foreign Application Priority Data

Jul. 6, 1978 [CH] Switzerland .......................... 7360/78

[51] Int. Cl.$^3$ .............................................. C07C 47/21
[52] U.S. Cl. .................................... 568/448; 426/534
[58] Field of Search ......................................... 568/448

[56] References Cited

U.S. PATENT DOCUMENTS

| | | | |
|---|---|---|---|
| 3,857,834 | 12/1974 | Nagata et al. | 568/448 |
| 3,914,451 | 10/1975 | Schrieber et al. | 568/448 |
| 4,324,809 | 4/1982 | Pickenhagen et al. | 426/534 |

FOREIGN PATENT DOCUMENTS 37584  4/1981  European Pat. Off. ............ 568/448

*Primary Examiner*—Werren B. Lone
*Attorney, Agent, or Firm*—Pennie & Edmonds

[57] ABSTRACT

Use of certain α,β-unsaturated aldehydes as flavoring and taste-modifying agents in the aromatization of foodstuffs in general and imitation flavors for foodstuffs, beverages, animal feeds, pharmaceutical preparations and tobacco products.

Some of the disclosed aldehydes are new chemical entities.

1 Claim, No Drawings

α,β-UNSATURATED ALDEHYDES AND USE OF SAME AS FLAVORING INGREDIENTS

This is a division of application Ser. No. 51,506 filed June 25, 1979, now U.S. Pat. No. 4,324,809, issued on Apr. 13, 1982.

TECHNICAL FIELD

The compounds to which the present invention relates belong to the class of α,β-unsaturated aldehydes of formula

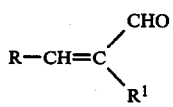

wherein symbol R represents a linear alkyl radical having 3 to 6 carbon atoms and $R^1$ represents a linear or branched alkyl radical having 1 to 7 carbon atoms.

Some of the compounds of formula (I) are new. These include the following:
2-butyl-hept-2-enal,
2-propyl-oct-2-enal,
2-pentyl-oct-2-enal and
2-butyl-non-2-enal.

The compounds of formula (I) possess interesting organoleptic properties and consequently may be advantageously used in the flavor industry.

BACKGROUND OF THE INVENTION

Numerous aldehydic compounds are known in the art. For instance, dec-2-enal is employed in the reconstitution of flavors of fruity type, especially of citrus fruits, or in the manufacture of peach type aromas. Certain lower alkyl α,β-unsaturated aldehydes, such as hex-2-enal, namely, in its trans isomeric form, are used in compositions of strawberry, banana, apple or apricot type. Other unsaturated aldehydes having the double bond in the β,γ- or γ,δ-position find an advantageous utilization in the reconstitution of creamy and fatty notes. Hept-4-enal belongs to this class of derivatives.

U.S. Pat. No. 3,914,451 describes the use as flavoring ingredient of 2-butyl-but-2-enal, a compound possessing a gustative taste of sweet, slightly roasted and fatty character, reminiscent of hazelnuts.

SUMMARY OF THE INVENTION

We have now surprisingly discovered that the compounds of formula (I) develop various gustative notes ranging from fatty notes to burnt, meaty, caramel or sometimes green and animal ones.

The class of compounds of formula (I) include 2-methyl-oct-2-enal, which possesses a particularly powerful flavor note of meaty type associated with an oily, green gustative character. For certain of its characters, the flavor of 2-methyl-oct-2-enal is reminiscent of the taste of potatoes when freshly subjected to frying or, more generally, of fried foodstuffs.

These features are also shown, although to a lesser extent, by the higher homologs of 2-methyl-oct-2-enal, viz. 2-butyl-oct-2-enal, 2-pentyl-oct-2-enal and 2-methyl-non-2-enal. Due to their valuable flavoring properties, the compounds of formula (I) can be used for the aromatization of foodstuffs and beverages of various natures. Typically, they can be used to impart, improve or modify the meaty and fatty notes of meat or meat imitating products destined for human or animal consumption.

Consequently, the present invention relates to a method for imparting, improving or modifying the organoleptic properties of foodstuffs and beverages, which comprises adding thereto a small but flavoring effective amount of at least one of the α,β-unsaturated aldehydes of formula (I).

The invention further provides a composition comprising a foodstuff or a beverage and a small but flavoring effective amount of at least one of the α,β-unsaturated aldehydes of formula (I).

An object of the present invention is also to provide a flavoring composition containing a flavoring effective amount of at least one of the α,β-unsaturated aldehydes of formula (I).

Another object of the instant invention is to provide a foodstuff or a beverage having a meaty taste due to the addition, as flavoring effective ingredient, of an α,β-unsaturated aldehyde of formula (I).

Still another object of the present invention is to provide a method to impart, improve or modify the oily-green gustative note of foodstuff subjected to a frying process which comprises adding thereto as flavoring effective ingredient at least one of the α,β-unsaturated aldehydes of formula (I).

The invention also provides the following new compositions of matter belonging to the class of α,β-unsaturated aldehydes of formula (I):
2-butyl-hept-2-enal,
2-propyl-oct-2-enal,
2-pentyl-oct-2-enal and
2-butyl-non-2-enal.

PREFERRED EMBODIMENTS OF THE INVENTION

In above given formula (I), symbol R represents a linear alkyl radical having 3 to 6 carbon atoms. Thus, R can represent a propyl, a butyl, a pentyl or a hexyl radical. Preferably, R designates a pentyl radical.

Symbol $R^1$ in formula (I) represents a linear or branched alkyl radical having 1 to 7 carbon atoms. Thus $R^1$ can designate a radical such as methyl, ethyl, propyl, iso-propyl, butyl, sec-butyl, ter-butyl, isobutyl, pentyl, isopentyl, neopentyl, ter-pentyl, hexyl, sec-hexyl, ter-hexyl, iso-hexyl, heptyl, sec-heptyl, ter-heptyl and iso-heptyl. Methyl is preferred.

The proportions at which the compounds can achieve interesting gustative effects vary within wide limits.

Preferably, these proportions are of from about 0.01 to 10 ppm (parts per million) by weight based on the total weight of the material into which they are incorporated. These values, however, should not be interpreted restrictively and it should be understood by those skilled in the art that concentrations lower or higher than those indicated above may be used whenever it is desired to achieve special effects. It is, moreover, well known in the art that concentrations of a given flavorant depend on the nature of the specific material it is desired to be aromatized and on the nature of the co-ingredients in a given composition.

The compounds of formula (I) can be utilized in accordance with the invention alone or, more frequently, in admixture with common edible solvents, e.g. in admixture with ethyl alcohol, dipropylene glycol or triacetine. Compounds (I) can be prepared in accordance with current methods, e.g. by aldol condensation of the appropriate saturated aldehydes or by cleavage of certain Schiff bases following the method described below for the preparation of 2-methyl-oct-2-enal (temperatures in degrees centigrade). This method, known as the Wittig type aldolization, has been described, for example, in "Neuere Methoden der Präparativen organischen Chemie", vol. VI, Editor W. Forst, Verlag Chemie, pp. 56–7.

Preparation of 2-methyl-oct-2-enal 1. 30 ml of a 1.62 N solution of butyllithium in hexane were added under stirring at room temperature and within 25 minutes to a solution of 5 g of diisopropylamine in 25 ml of anhydrous ether. The reaction mixture was then cooled at 0° and, in 10 minutes time, 6.95 g of the Schiff base obtained by reacting cyclohexylamine and propenal, in 40 ml diethyl ether, were added thereto. The obtained mixture was kept at 0° for 10 additional minutes, then cooled at −70°, at which temperature 5 g of hexanal were added dropwise. The temperature was slowly increased to room temperature, while the mixture was kept under continuous stirring, then it was poured onto 50 g of crushed ice and extracted with 3 fractions of 50 ml each of ether. The combined organic extracts were washed with water and with a 10% aqueous HCl solution until neutrality. After drying and evaporation at 40° they gave 10.9 g of a residue which could be directly utilized for the next reaction step.

2. A mixture comprising 10.9 g of the product obtained according to paragraph 1 above, 25 ml of ethanol, 25 ml of water and 25 ml of 10% sulfuric acid was refluxed for 3 hours, then cooled and extracted with 4 fractions of 30 ml each of ether. The combined organic extracts were washed, dried and evaporated at 20° to give 5.6 g of a residue which, upon distillation, yielded 3.1 g of 2-methyl-oct-2-enal. The analytical data of the thus obtained product were identical with those of a pure sample prepared in accordance with the literature (see e.g.: Tetrahedron Letters, 1973, 2465–8). The other compounds of formula (I) could be prepared in an analogous manner.

The new compounds of the invention have shown the following analytical data:

2-Butyl-hept-2-enal:
MS: M+ =168; m/e: 55 (100), 41 (84.2), 111 (83.5), 43 (75.7), 83 (56.8), 139 (55), 81 (48.3).
NMR(CDCl$_3$): 0.90–1.0(6H, 2t); 1.32 (8H, m); 2.25 (4H, m); 6.40 (1H, t); 9.30 (1H, s) δ ppm.

2-Propyl-oct-2-enal
MS: M+ =168; m/e: 55 (100), 41 (93), 125 (92.5), 43 (78), 83 (69), 29 (59.5), 69 (49), 97 (45.5).
NMR(CDCl$_3$): 0.90 (3H, t); 1.0 (3H, t); 1.4 (8H, m); 2.27 (4H, m); 6.57 (1H, t); 9.38 (1H, s) δ ppm.

2-Pentyl-oct-2-enal
MS: M+ =196; m/e: 55 (100), 41 (97.6), 125 (83.3), 43 (78), 29 (70.0), 83 (68.2), 69 (59), 56 (59), 81 (57.8), 153 (52), 95 (50.2), 97 (46.8).
NMR(CDCl$_3$): 0.89–0.91 (6H, 2t); 1.32 (12H, m); 2.30 (4H, m); 6.44 (1H, t); 9.38 (1H, s) δ ppm.

2-Butyl-non-2-enal
MS: M+ =196; m/e: 55 (100), 41 (89.5), 43 (86.7), 139 (84.1), 83 (62), 69 (59.3), 29 (53), 97 (49.2), 71 (49.2).
NMR(CDCl$_3$): 0.84 (6H, t); 1.22–1.53 (12H, m); 2.10–2.55 (4H, m); 6.42 (1H, t); 9.35 (1H, s) δ ppm.

The invention is further illustrated by the following examples.

EXAMPLE 1

A series of compounds belonging to the class of α,β-unsaturated aldehydes of formula (I) were evaluated by dissolving them in an aqueous salt solution (0.5% NaCl in crystal spring water). The following Table summarizes the opinion expressed by the experienced flavorists who conducted the evaluation:

TABLE I

| Compound | Dosage [ppm] | Evaluation comments |
| --- | --- | --- |
| 2-propyl-hept-2-enal | 1.0 | fatty, meaty, slightly floral |
| 2-butyl-hept-2-enal | 2.0 | meaty, burnt, caramel |
| 2-methyl-oct-2-enal | 0.2 | fatty, meaty, oily, green, powerful |
| 2-propyl-oct-2-enal | 2.0 | meaty, sweet, caramel, animal |
| 2-butyl-oct-2-enal | 2.0 | green, fatty, oily, animal |
| 2-pentyl-oct-2-enal | 2.0 | fatty, vegetable, animal |
| 2-hexyl-oct-2-enal | 1.0 | meaty, burnt, fatty, green |
| 2-heptyl-oct-2-enal | 2.0 | fatty, acid, floral, sweet, oily, animal |
| 2-butyl-non-2-enal | 2.0 | slightly fatty acid, slightly green, oily, meaty |
| 2-pentyl-non-2-enal | 1.0 | fatty, slightly meaty |
| 2-methyl-non-2-enal | 0.2 | powerful fried oil character, fatty |

Other samples of compounds of formula (I) in their pure state were subjected to odor evaluation. The comments expressed by the testing panel are given hereinbelow.

TABLE II

| Compound | Evaluation comments |
| --- | --- |
| 2-propyl-hex-2-enal | fruity, floral, woody |
| 2-pentyl-hex-2-enal | fruity, strawberry like |
| 2-ethyl-hept-2-enal | fatty, floral |
| 2-hexyl-hept-2-enal | fruity, citrus fruit, mandarin |
| 2-pentyl-non-2-enal | fatty, animal |
| 2-methyl-non-2-enal | fruity, fishy, oily |
| 2-isopropyl-oct-2-enal | fatty, green |
| 2-hexyl-non-2-enal | fatty |

EXAMPLE 2

A reconstituted beef broth was prepared by mixing together the following ingredients (parts by weight):

| | |
| --- | --- |
| Commercial beef extract | 10 |
| Monosodium glutamate | 1 |
| 50:50 Mixture of sodium inositate: sodium guanilate | 0.005 |
| Sodium chloride | 8 |
| Lactic acid | 0.5 |
| Water | 980.485 |
| | 1,000.000 |

Samples of the thus prepared broth were flavored using the following ingredients at the given concentrations and were then subjected to an organoleptic evaluation by comparison with an unflavored sample.

TABLE III

| Compound | Dosage [ppm] | Evaluation comments |
| --- | --- | --- |
| 2-propyl-hept-2-enal | 2.0 | more meaty, fatty, burnt |
| 2-butyl-hept-2-enal | 3.0 | greener, fattier, reminiscent of chicken |

TABLE III-continued

| Compound | Dosage [ppm] | Evaluation comments |
| --- | --- | --- |
| 2-methyl-oct-2-enal | 0.05 | fat<br>more meaty, chicken character |
| 2-propyl-oct-2-enal | 3.0 | more burnt, caramel character |
| 2-butyl-oct-2-enal | 3.0 | more pronounced meaty and fatty character |
| 2-pentyl-oct-2-enal | 3.0 | fattier, tallow character |
| 2-hexyl-oct-2-enal | 2.0 | more meaty, chicken, chicken fat |
| 2-heptyl-oct-2-enal | 3.0 | fatty broth character |
| 2-butyl-non-2-enal | 3.0 | animal, burnt |

EXAMPLE 3

A beef broth was prepared according to Example 2 and samples thereof were evaluated as usual by comparison with an unflavored sample. The Table below summarizes the results of the evaluation.

TABLE IV

| Compound | Dosage [ppm] | Evaluation comments |
| --- | --- | --- |
| 2-pentyl-non-2-enal | 2.0 | more meaty |
| 2-methyl-non-2-enal | 0.05 | powerful oily taste, fatty, fried oil |

EXAMPLE 4

A sample of commercial hydrogenated vegetable oil having a bland taste was flavored with 2-methyl-non-2-enal at a concentration of 0.50 ppm.

Extruded corn snacks were manufactured by using a base of 75% corn and 25% dehydrated potato powder and coated with the flavored oil in the following proportions:

| | |
| --- | --- |
| extruded snacks | 80 g |
| flavored oil | 20 g |
| | 100 g (Sample A) |

A second sample of identical corn snacks was coated in the same proportions with unflavored oil (sample B). The two samples were evaluated organoleptically.
Comments:
odor: sample A was more oily and more fried in character than B.
flavor: sample A was more fried in character.

The tasters were unanimous in considering that sample A possessed a more typical French fries character.

What we claim is:
1. An α-β-unsaturated aldehyde selected from the group consisting of:
2-butyl-hept-2-enal
2-propyl-oct-2-enal
2-pentyl-oct-2-enal and
2-butyl-non-2-enal.

* * * * *